United States Patent
Zimmerman

(10) Patent No.: US 12,220,346 B2
(45) Date of Patent: Feb. 11, 2025

(54) APPLICATOR WITH THERMAL CONTACT SENSORS

(71) Applicant: LIGHTFECTIVE LTD., Caesarea (IL)

(72) Inventor: Yotam Zimmerman, Hadera (IL)

(73) Assignee: LIGHTFECTIVE LTD., Caesarea (IL)

(*) Notice: Subject to any disclaimer, the term of this patent is extended or adjusted under 35 U.S.C. 154(b) by 1177 days.

(21) Appl. No.: 17/029,218

(22) Filed: Sep. 23, 2020

(65) Prior Publication Data

US 2021/0153349 A1  May 20, 2021

Related U.S. Application Data

(60) Provisional application No. 62/935,696, filed on Nov. 15, 2019.

(51) Int. Cl.

| *A61F 7/00* | (2006.01) |
| *A61B 18/00* | (2006.01) |
| *A61B 18/18* | (2006.01) |
| *A61N 5/06* | (2006.01) |
| *H05K 1/02* | (2006.01) |
| *A61F 7/02* | (2006.01) |
| *H05K 1/11* | (2006.01) |
| *H05K 1/16* | (2006.01) |

(52) U.S. Cl.
CPC ............... *A61F 7/00* (2013.01); *A61B 18/18* (2013.01); *A61N 5/0616* (2013.01); *A61N 5/0625* (2013.01); *H05K 1/028* (2013.01); *A61B 2018/00011* (2013.01); *A61B 2018/00023* (2013.01); *A61B 2018/00041* (2013.01);

(Continued)

(58) Field of Classification Search
CPC ............... A61F 7/00; A61F 2007/0052; A61F 2007/0054; A61F 2007/0056; A61F 2007/0073; A61F 2007/0095; A61F 2007/0282; A61F 2007/029; A61B 18/18; A61B 2018/00011; A61B 2018/00023; A61B 2018/00041; A61B 2018/00089; A61B 2018/00095; A61B 2018/00452; A61B 2018/00464; A61B 2018/00642; A61B 2018/00702; A61B 2018/00714; A61B 2018/00791; A61B 2018/00815; A61B 2018/00821; A61B 2018/00886; A61B 2018/00648; A61B 18/203; A61B 2018/1807; A61B 2090/065; A61N 5/0616; A61N 5/0625; A61N 2005/0643; A61N 2005/066; H05K 1/028; H05K 1/0201; H05K 1/111; H05K 1/16; H05K 2201/10151; H05K 1/0209; H05K 3/0061; H05K 2201/0999; H05K 1/0393; Y02P 70/50

See application file for complete search history.

(56) References Cited

U.S. PATENT DOCUMENTS

| 6,086,247 A | 7/2000 | von Hollen |
| 6,354,297 B1 | 3/2002 | Eiseman |

(Continued)

FOREIGN PATENT DOCUMENTS

| WO | WO-2009059270 A1 * | 5/2009 | ........... A61N 5/0616 |
| WO | WO2018211492 A1 | 11/2018 | |

*Primary Examiner* — Kaitlyn E Smith
*Assistant Examiner* — Ana Veruska Guerrero
(74) *Attorney, Agent, or Firm* — Paul Katterle

(57) ABSTRACT

Disclosed is a thermal contact sensor for use in aesthetic skin by heat treatment for altering the aesthetic appearance of a subject. The thermal contact sensor measures the difference in sensor temperature when in contact or absence of contact with the skin and automatically operates a source of optical radiation to heat the skin.

10 Claims, 7 Drawing Sheets

(52) U.S. Cl.
CPC ............... *A61B 2018/00089* (2013.01); *A61B 2018/00095* (2013.01); *A61B 2018/00452* (2013.01); *A61B 2018/00464* (2013.01); *A61B 2018/00642* (2013.01); *A61B 2018/00702* (2013.01); *A61B 2018/00714* (2013.01); *A61B 2018/00791* (2013.01); *A61B 2018/00815* (2013.01); *A61B 2018/00821* (2013.01); *A61B 2018/00886* (2013.01); *A61F 2007/0052* (2013.01); *A61F 2007/0054* (2013.01); *A61F 2007/0056* (2013.01); *A61F 2007/0073* (2013.01); *A61F 2007/0095* (2013.01); *A61F 2007/0282* (2013.01); *A61F 2007/029* (2013.01); *A61F 2007/0295* (2013.01); *A61N 2005/0643* (2013.01); *A61N 2005/066* (2013.01); *H05K 1/0201* (2013.01); *H05K 1/111* (2013.01); *H05K 1/16* (2013.01); *H05K 2201/10151* (2013.01)

(56) References Cited

U.S. PATENT DOCUMENTS

| | | | |
|---|---|---|---|
| 6,645,162 B2 | 11/2003 | Friedman et al. | |
| 6,673,096 B2 | 1/2004 | Lach | |
| 7,351,252 B2 | 4/2008 | Altshuler et al. | |
| 7,981,112 B1* | 7/2011 | Neev | A61B 18/08 607/98 |
| 8,160,691 B2 | 4/2012 | Jang et al. | |
| 9,770,292 B2* | 9/2017 | Moss | A61B 18/1206 |
| 2006/0287696 A1 | 12/2006 | Wright et al. | |
| 2007/0129711 A1 | 6/2007 | Altshuler et al. | |
| 2008/0200969 A1* | 8/2008 | Weber | A61N 1/06 374/E13.002 |
| 2008/0262574 A1 | 10/2008 | Briefs et al. | |
| 2010/0010484 A1* | 1/2010 | Mehta | A61B 18/14 606/34 |
| 2011/0098789 A1* | 4/2011 | Weckwerth | A61N 5/0616 607/88 |
| 2013/0018236 A1* | 1/2013 | Altshuler | A45D 26/0061 600/306 |
| 2013/0123765 A1 | 5/2013 | Zarsky et al. | |
| 2014/0303608 A1* | 10/2014 | Taghizadeh | A61F 7/00 606/20 |
| 2014/0309628 A1* | 10/2014 | Vaynberg | A61B 18/1477 606/41 |
| 2016/0089202 A1 | 3/2016 | Schomacker et al. | |
| 2017/0304646 A1 | 10/2017 | Pryor et al. | |
| 2018/0271597 A1 | 9/2018 | Eisenmann et al. | |
| 2018/0303406 A1 | 10/2018 | McKinney et al. | |
| 2020/0197723 A1* | 6/2020 | Zimmerman | A61H 9/0057 |

* cited by examiner

APPLICATOR WITH THERMAL CONTACT SENSORS

CROSS-REFERENCE TO RELATED APPLICATION

This patent application claims the benefit of priority under 35 U.S.C. § 119(e) to Provisional Patent Application No. 62/935,696 filed on Nov. 15, 2019, which is incorporated herein by reference.

TECHNICAL FIELD

The applicator relates to the field of aesthetic skin by heat treatment, and in particular, to treatment for altering the aesthetic appearance of a subject.

BACKGROUND

There are several methods related to a change in the aesthetic appearance of a portion of a subject body. Most of the methods use heat to reduce or redistribute subcutaneous fat, also known as adipose tissue. Heat damages the fat cells so that lipids contained within the fat cells or adipose tissue can escape. A portion of the lipids is carried away from a treated skin segment and disposed of by lymphatic organs of the object.

There is a variety of devices constructed to apply energy to a subject skin. The applied energy transforms into heat and heats a desired segment of the subcutaneous fat. Such devices could apply to the skin radio frequency (RF), ultrasound, and light or optical radiation, for example, light generated by a coherent or noncoherent light source. Although it is desirable to apply the heat directly to the subcutaneous fat, almost all known devices apply the energy through the upper layers of the skin and consequently heat the upper layers of the skin. Because of this, almost all devices have different arrangements that cool the skin and upper layers of the skin.

Patent Cooperation Treaty application No. IL2018/050484 to the same inventor and assignee discloses a method and apparatus for subcutaneous fat by light treatment. The light wavelengths selected are transmitted through the skin and almost do not affect it. Each treatment session continues for about 10 minutes. The skin and upper skin layers in the course of a skin treatment session, absorb a certain amount of light energy and a cooling arrangement cools the skin.

Typical applications of the skin by optical radiation treatment include wound healing, cellulite reduction, skin rejuvenation, fat reduction, and subject body contouring. Existing publications show that subcutaneous fat reduction by short with a duration of milliseconds to seconds energy pulses requires significant energy. The fluence of the optical energy could be up to 80 J/cm2 without causing severe dermal damage or scarring, but the temperature developed in the skin is not bearable by the subject.

Methods of applying a lower optical energy fluence for a longer time are known. For example, US Patent Publication No. 2018/0271597 discloses a method of the skin by optical radiation treatment where the treatment session continues 20 to 60 min.

The following patents and patent publications disclose different methods of skin treatment by light: U.S. Pat. No. 6,086,247 to van Hollen, U.S. Pat. No. 8,160,691 to Jang, U.S. Pat. No. 7,351,252 to Altshuler, US 20070129711 to Zenzie, US20080262239 to Prior, US20160089202 to Schomacker, US20170304646 to Pryor, US20180271597 to Eisenmann, and US20180303406 to McKinney.

SUMMARY

The present disclosure is directed to an applicator and method of manipulating subdermal fat to cause a desired aesthetic skin treatment effect. The applicator includes: a stainless steel frame maintained at a temperature of 15 degrees C. and a transparent sapphire window in thermal communication with the metal frame. A matrix of optical radiation-emitting elements, such as LEDs or diode lasers mounted behind the transparent window, and at least one thermal contact sensor. The LEDs, organized in a matrix type layout, emit optical radiation from 800 to 1100 nm. The thermal contact sensor operates to detect a presence of contact between the metal frame and transparent window with the subject skin. The applicator also includes an internal processor or is in communication with a CPU of an external computer. The computer is configured to measure the temperature, the power and the time it takes to a heater to raise the thermal contact sensor temperature from 15 degrees C. to 38 degrees C.

The thermal contact sensor is a stainless steel cup-like housing with a bottom thinner than other housing walls. The thermal contact sensor includes at least one temperature sensor and a heater. The temperature sensor, could be a thermistor or a thermocouple, and heater that is a resistor, are mounted on separate enhanced pads of a flexible printed circuit board. A thermally conductive glue attaches the flexible board and enhanced pads to cup-like housing.

The thermal contact sensor 300 could operate in three operation modes: one mode of operation of the thermal contact sensor is based on the temperature of the skin and stainless steel frame measurements. Another mode of operation of the thermal contact sensor is based on the measurement of power supplied to the thermal contact sensor. An additional mode of operation of the thermal contact sensor is based on the measurements of the difference in the thermal inertia of the thermal contact sensor in idle state and in contact with the skin. In all operation modes the stainless steel frame, sapphire window, and thermal contact sensor securely and firmly the attached to the subject skin.

BRIEF DESCRIPTION OF THE DRAWINGS

The features and advantages of the present applicator and method of its use will be understood and appreciated more fully from the following detailed description, taken in conjunction with the drawings in which identical referral numbers mark identical or similar elements.

DETAILED DESCRIPTION OF ILLUSTRATIVE EMBODIMENTS

Definitions

As used in the current disclosure, the term "subject" is meant a human or non-human animal (e.g., a mammal).

The term "skin" or "tissue" as used in the present disclosure includes the outer skin layers such as stratum corneum, dermis, epidermis, and the deeper subcutaneous layers such as fat or adipose tissue.

The term "skin treatment energy," as used in the present disclosure, means optical energy facilitating the achievement of a desired skin treatment effect.

The term "energy to skin applying element" as used in the present disclosure means an element operative to receive skin treatment energy from a source of such energy and couple or apply the received energy to a treated segment of skin. A source of light could be such an element.

Electromagnetic radiation application to biological tissue, and in particular optical radiation application to skin or tissue, generates heat in the tissue. The heat could be sufficient to reduce the number of fat cells in subcutaneous tissue. Optical radiation application to skin supports the selective heating of the subcutaneous fat or adipose tissue region to destroy fat tissue. The treatment could be implemented to destroy fat tissue and avoid damaging the dermis and epidermis.

Patent Cooperation Treaty application No. IL2018/050484 to the same inventor and assignee discloses a method and applicator for subcutaneous fat by light treatment. The light wavelengths selected are transmitted through the skin and almost do not affect it. Each treatment session continues for about 10 minutes. The skin and upper skin layers in the course of a skin treatment session, absorb a certain amount of light energy and a cooling arrangement cools the skin.

The period of application of light energy to the subject skin or tissue is relatively long and accompanied by some skin temperature changes, and accurate temperature control could favorably affect the skin treatment. The present application provides a thermal contact sensor and method for accurate skin temperature control.

Figure 1:
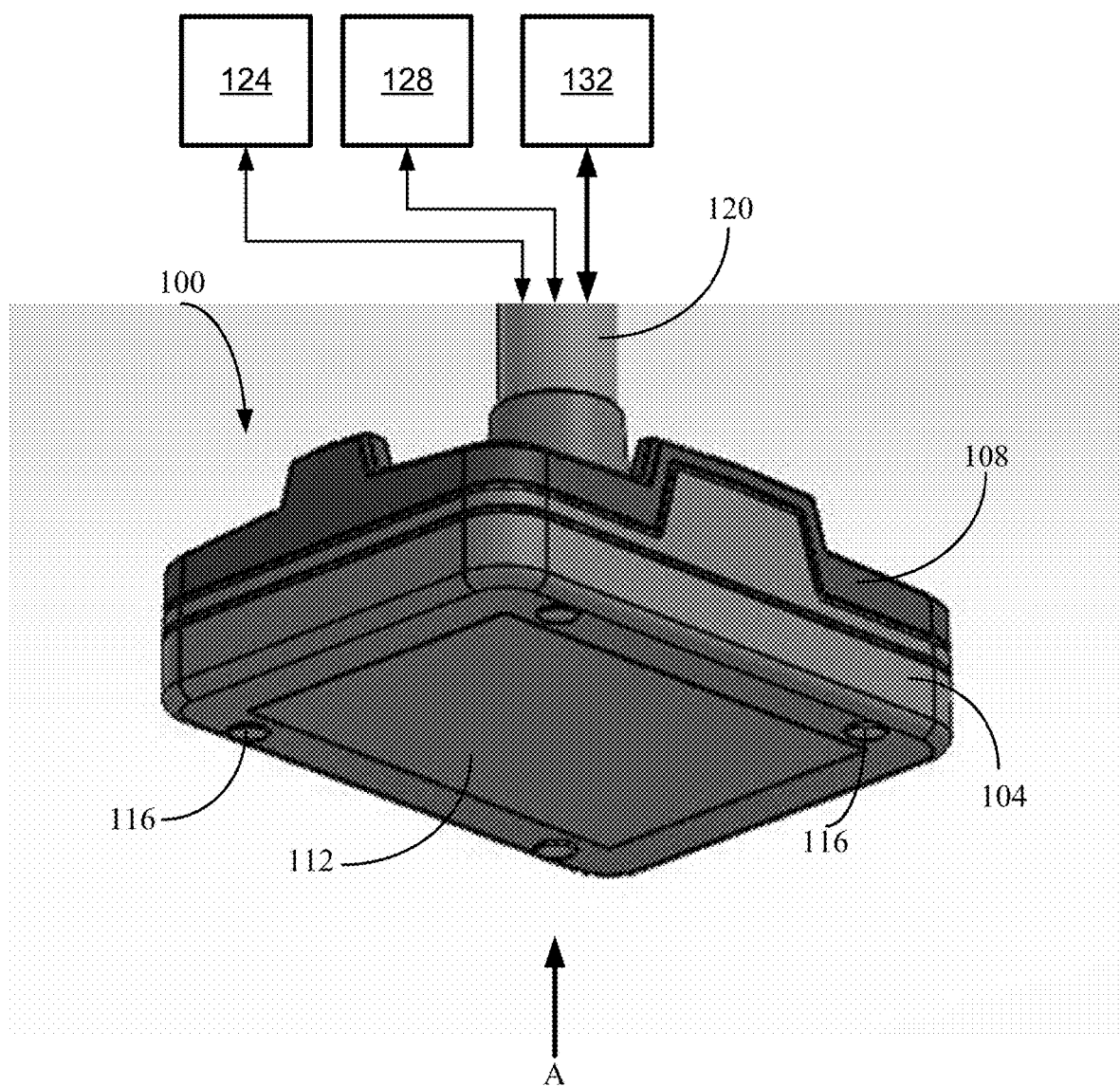
FIG. 1 is a three-dimensional representation of an example the present applicator for skin treatment.
Figure 2:
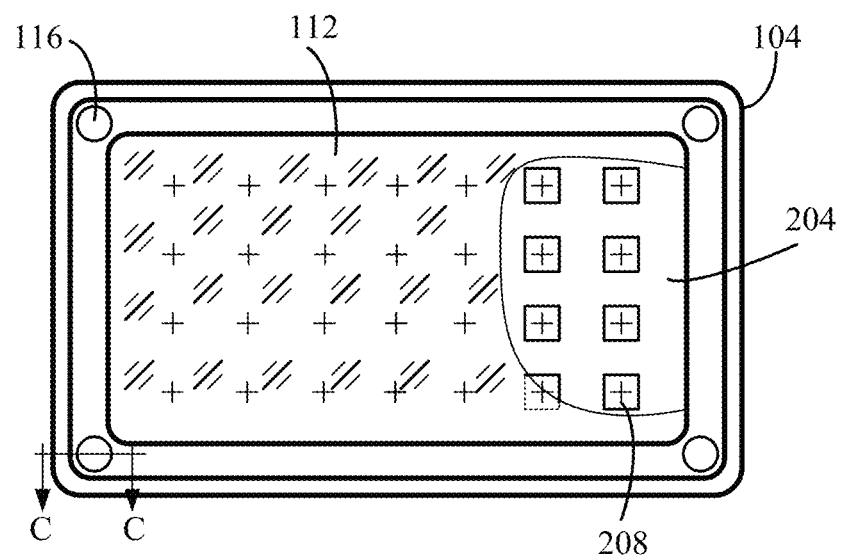
FIG. 2 is a bottom view of an example of the applicator of FIG. 1.

FIG. 1 is a three-dimensional representation of an example of the present applicator for skin treatment. Applicator 100 includes a frame 104 made of a heat and cold conducting material, for example, metal. Stainless steel is a good heat/cold conductor, and when applied to a subject skin, stainless steel is biocompatible and does not cause adverse skin effects. A plastic or other similar material cover 108 covers stainless steel frame 104 and forms a volume inside which, as it will be explained below, a plurality of semiconductor light sources such as LEDs or diode lasers are mounted on a printed circuit board 204 (FIG. 2). A thermoelectric cooling unit (not shown) could also be mounted inside the volume. A transparent window 112 transmitting the light emitted by the light sources is in thermal communication with stainless steel frame 104. Sapphire or quartz are materials from which window 112 is made. Several spaced apart thermal contact sensors 116 are inserted into stainless steel frame 104. The current design illustrates four thermal contact sensors 116, although the number of thermal and contact sensors 116 could be different, for example, two or eight or any other number sufficient to fulfill the task of accurate contact temperature detection and measurement. Sensors 116 are in thermal communication with stainless steel frame 104. An umbilical cable 120 provides communication between the light sources, and their power supplies 124. Umbilical cable 120 also collects thermal contact sensors 116 readings and transmits the readings to a processor. In one example, the processor is mounted inside applicator 100. In another example, a personal computer 128 CPU could be used.

Typically, stainless steel frame 104 could include coolant conducting channels. A cooling unit 132 supplies coolant through tubing included in umbilical cable 120. The cooled stainless steel frame is in thermal contact with sapphire window 112. The stainless steel frame cools the sapphire window and the skin or tissue area with which the sapphire window is in contact.

FIG. 2 is a bottom view of an example of the applicator of FIG. 1. Beneath transparent window 112 is located a rigid printed circuit board 204. A matrix of semiconductor light sources such as LEDs is mounted on printed circuit board 204. LEDs 208 provide optical or treatment radiation. LEDs 208 arranged in a matrix could have different layouts, for example, 2×2, configuration, 3×5, 7×9, or any other layout.

LEDs 208 could be of any type and packaging, such as COB (Chip on Board) SMD (Surface Mounted Diode), or regular bulb-like packaging. In some examples, diode lasers could be used instead of LEDs. LEDs 208 emit infrared optical radiation with a wavelength of 850 nm to 1100 nm. LED 208 could provide infrared optical radiation sufficient to irradiate the skin with the power of 0.5 Watt/sq. cm to 5.0 Watt/sq. cm and typically would provide infrared optical radiation sufficient to irradiate the skin with a power of 0.8 to 1.4 Watt/sq. cm. Sapphire window 112 transmits the optical radiation to the tissue. Pressure applied to the applicator by any known means supports proper thermal contact without voids between sapphire window 112 and the tissue. The pressure also facilitated a good thermal contact between the skin or tissue and cooled sapphire window 112, and stainless steel frame 104.

In the course of the skin treatment, applicator 100 (FIG. 1) maintains the skin and outer layers of the skin or tissue at a safe temperature. The heat generated by the outer skin layers absorption of the IR radiation is removed by conduction to cold sapphire window 112 and stainless steel frame 104. Several thermal contact sensors 116 built-in stainless steel frame 104 support monitoring of skin temperature to maintain safety skin treatment temperature.

Figure 3A:
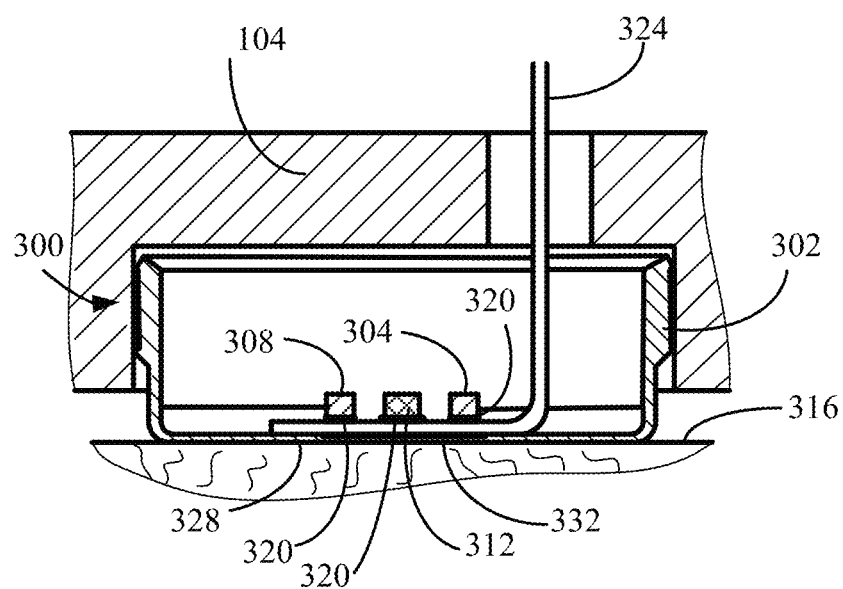
FIG. 3A is a cut-through of an example of the stainless steel frame and a thermal contact sensor.

FIG. 3A is a cut-through of an example of the stainless frame and a thermal contact sensor. The thermal contact sensor 300 contains a first temperature sensor 304 and a second temperature sensor 308, and a heat-generating element 312, which could be a regular resistor. A temperature sensor could be a commercially available thermistor or a thermocouple. Each of the spaced-apart temperature sensors 304 and 308 is attached to a heat-conducting substrate, which is an enhanced copper solder coated pad 320 of the flexible printed circuit board 324. Resistor 312 is also attached to a corresponding separate enhanced copper solder coated pad 320 of the flexible printed circuit board 324. The flexible printed circuit is made of standard 12.5-80 microns thick Kapton® (polyimide film). The heat-conducting substrate or enhanced copper solder coated pad could be a standard 0.5 to 2 oz thick copper layer (0.089 to 0.203 mm).

Enhanced sensor and resistor solder coated copper-pad mounting structure is further in thermal communication with surface 328 of a can-like sensor housing 300 and supports almost real-time temperature reading. A thermal conductive glue could further enhance thermal communication of enhanced pads 320 with surface 328 of a can-like sensor housing 300.

Figure 3B:
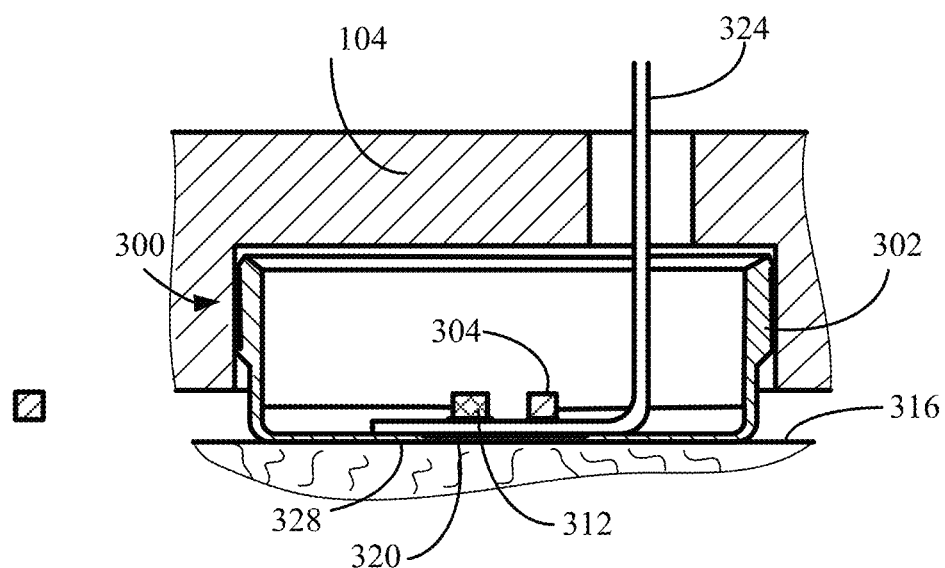
FIG. 3B is a cut-through of another example of the stainless steel frame and a thermal contact sensor.
Figure 4:
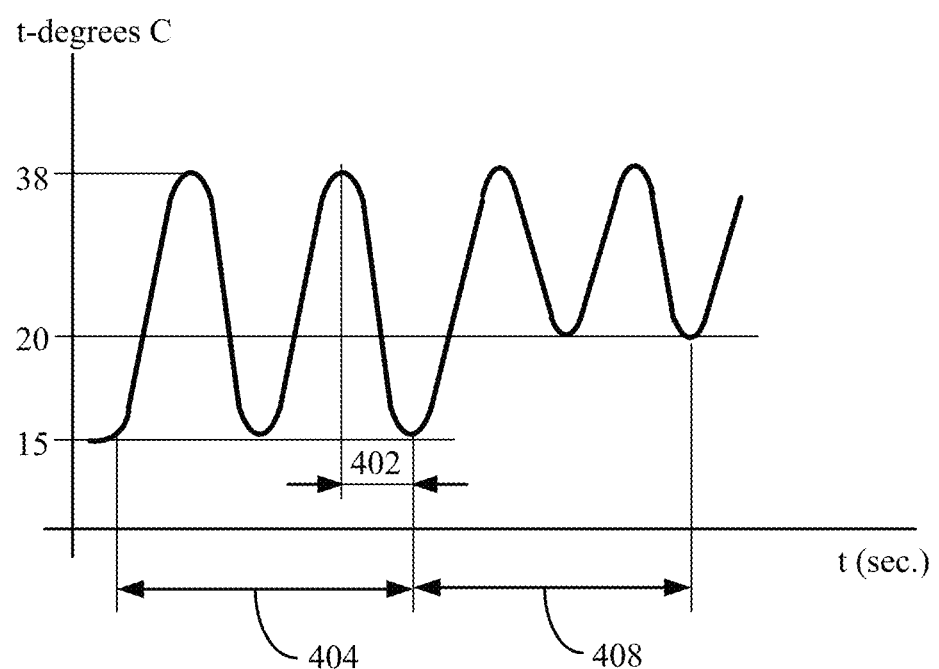
FIG. 4 is a schematic illustration of an example of a thermal contact sensor operation.
Figure 5:
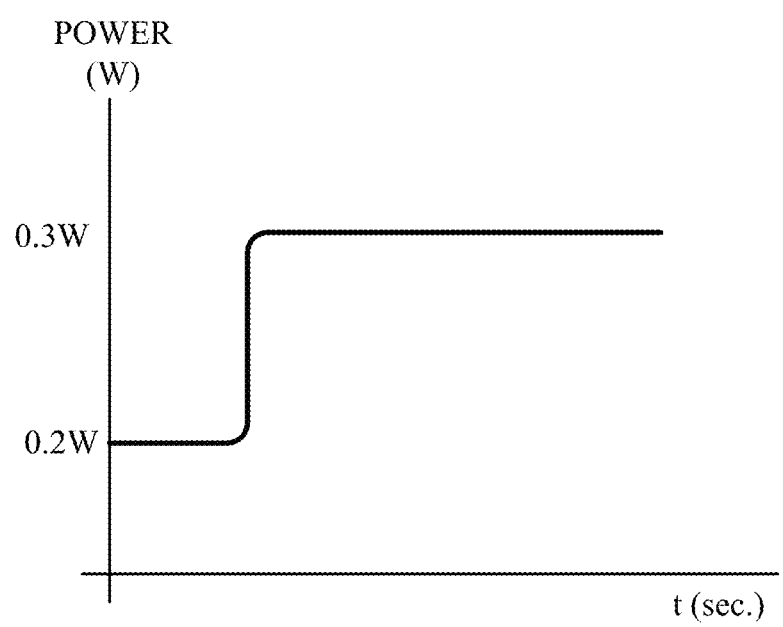
FIG. 5 is a schematic illustration of another example of a thermal contact sensor operation.

FIG. 3B is a cut-through of another example of the stainless steel frame and a thermal contact sensor. The thermal contact sensor 300 contains one temperature sensor 304, and a heat-generating element 312, which could be a regular resistor. A temperature sensor could be a commercially available thermistor or a thermocouple. The temperature sensor 304 and second temperature sensor 308 are attached to a respective heat-conducting substrate, which is an enhanced copper solder coated pad 320 of the flexible printed circuit board 324. The flexible printed circuit is made of standard 12.5-80 microns thick Kapton® (polyimide film). The heat-conducting substrate or enhanced copper solder coated pad could be standard 0.5 to 2 oz copper coating (0.089 to 0.203 mm thick).

Enhanced temperature sensor and resistor solder coated copper-pad mounting structure is further in thermal communication with surface 328 of a can-like sensor housing 300 and supports almost real-time temperature reading. A thermally conductive glue 332 could further enhance thermal communication of enhanced pads 320 with surface 328 of a can-like sensor housing 300.

The thermal contact sensor 300 can-like housing 302 is made of stainless steel and is in thermal communication with stainless steel frame 104 and skin 316. Thermally conductive contact of can-like housing 302 of sensor 300 with stainless steel frame 104 could be achieved by pressing can-like sensor housing 302 into a receiving hole of stainless frame 104 or using a thermally conductive glue to connect between them. Sensor 300 can-like housing 302 wall or bottom 328, which is in contact with flexible circuit board 324, is thinner than other housing walls and is about 60 to 100 micron or less thin, and the thermal resistance of wall 328 is relatively low. Thermally conductive adhesive 332 could be used to coat all can-like contact surfaces being in contact with stainless steel frame 104 and improve thermal communication between the surfaces.

The first temperature sensor 304 and second temperature sensor 308 are in thermal communication with subject skin or tissue 316, and at the same time with a cooled stainless steel frame 104. The thermal resistance between thermistors 304 and 308 or only thermistor 304 and sensor and skin surface 316 is relatively small, as compared to the thermal resistance between thermistors 304 and 308, and stainless steel frame 104.

The thermal contact sensor 300 could operate in three operation modes:

Operation of thermal contact sensor 300 based on the temperature of the skin and stainless steel frame 104 measurements;

Operation of thermal contact sensor 300 based on the measurement of power supplied to the thermal contact sensor; and Operation of thermal contact sensor 300 based on the difference in the thermal inertia of the sensor 300 in idle state and contact with the skin.

Operation of thermal contact sensor 300 based on the temperature of the skin and stainless steel frame 104 measurements.

In the course of skin treatment the stainless steel frame 104, sapphire window 112, and thermal contact sensors 300 are secure and firmly attached to skin 316. When in contact with skin 316, thermal contact sensor 300 measures temperature that is higher than the temperature of stainless steel frame 104 and lower than the temperature of skin or tissue 316. When the contact between sensor 300 and skin 316 is absent, sensor 300 is in thermal contact only with stainless steel frame 104 (idle state). In the absence of contact with skin 316, sensor 300 is measuring only the stainless steel frame 104 temperature. To support rapid sensing of temperature by sensor 300, the difference between the presence of contact with skin 316 and absence of contact with skin 316, CPU 128 operates heat-generating element 312 to maintain a definite temperature difference between skin 316 and stainless steel frame 104. For example, if the sensed temperature is 20 degrees C. or more, the sensor indicates the presence of contact with skin 316. If the sensed temperature is 15 degrees C. or less, the sensor indicates on absence of contact with skin 316.

If the stainless frame 104 temperature is 15 degrees C., CPU 128 operates heat-generating element 312 to heat the thermal contact sensor to about 20 degrees C. The heat-generating element or resistor 312 operates in pulse mode, in a cycle where resistor 312 is "ON" for 2 sec and "OFF" for the next two seconds. At the time of the OFF cycle, thermistor 312 is sensing and transmitting the measured temperature.

Operation of thermal contact sensor 300 based on the measurement of power supplied to the thermal contact sensor.

In this operation mode, resistor 312 operates in closed-loop control mode to maintain, for example, a constant thermal contact sensor temperature of 38 degrees C.

When thermal contact of thermal contact sensor 300 with the skin 216 (FIG. 3) exists, the contact is characterized by the increase in electric power consumed by resistor 312. For example, in the absence of contact between thermal contact sensor 300 and skin 316, the power consumed by resistor 312 could be 0.2 Watt. When the consumed by resistor 312 power is growing, for example to 0.3 Watt, the growth in the consumed power means that thermal contact sensor 300 is in contact with skin 316. In the absence of contact between thermal contact sensor 300 and skin 316, the power supplied to resistor 312 could be reduced.

Operation of thermal contact sensor 300 based on the thermal inertia of the sensor 300 in idle state and in contact with the skin.

CPU 128 or internal processor could be built to measure the time it takes to resistor 312 to rise the thermal contact sensor 100 temperature from 15 degrees C. to 38 degrees C. CPU 128 measures the time elapsed from the activation of resistor 312 until thermal contact sensor 300 reaches the target temperature, for example, from 20 degrees C. to 35 degrees C. Heating is done every about 2 sec (it takes about 1 sec to cool from 38 degrees C. to 15 degrees C.).

Figure 6:
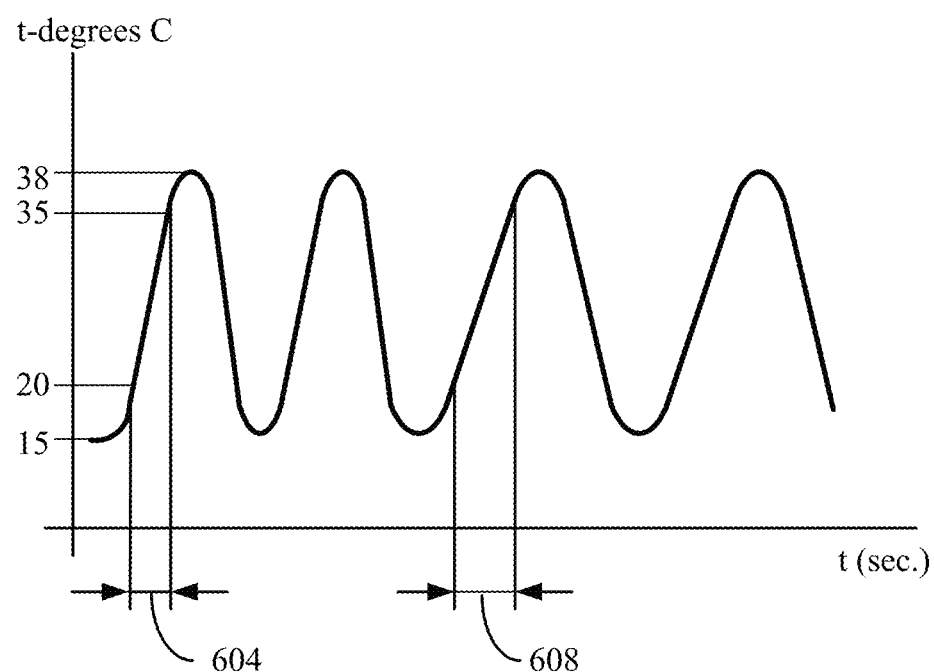
FIG. 6 is a schematic illustration of an additional example of a thermal contact sensor operation.

The time elapsed that takes resistor 312 to heat thermal contact sensor from 15 degrees C. to 38 degrees C. is a function of heated mass thermal inertia. In the absence of contact with the skin or tissue, the thermal mass of sensor 300 is relatively low, and the temperature rise is fast numeral 604 (FIG. 6). The rise time was measured to be about 400 msec (numeral 604). When thermal contact sensor 300 is in contact with skin 316, the thermal mass includes most close to the sensor 300 skin volume, and the thermal mass is large. The thermal contact sensor temperature rise is slow 608 and was measured to be 600 msec.

The present temperature contact sensor supports increased and transparent to the user ease of use and increased accuracy as compared to other known types of sensors.

The sensor supports accurate measurement of skin temperature in the treated skin area of a subject. The thermal contact sensor measures the thermal contact of the skin if the pressure of applicator is increased or decreased, and if the skin is wet or dry, the sensor will measure these changes.

The sensor operates as heatsink by accumulating or dissipating the heat produced by the resistor.

What is claimed is:

1. A method of thermal contact detection, comprising:
    applying to a skin of a subject an applicator containing a thermal contact sensor that comprises:
        a metal frame;
        a can-like housing having housing walls and a bottom which is thinner than the housing walls;
        at least one temperature sensor and a heater; and
        a flexible printed circuit board including enhanced solder coated pads configured to receive the at least one temperature sensor and the heater;
    operating the thermal contact sensor in one of a first mode, a second mode and a third mode to determine whether the thermal contact sensor is in contact with the skin of the subject;
    wherein operating the thermal contact sensor in the first mode comprises operating the heater to maintain a temperature difference between the skin and the metal frame;
    wherein operating the thermal contact sensor in the second mode comprises measuring power supplied to the thermal contact sensor; and
    wherein operating the thermal contact sensor in the third mode comprises measuring a difference in a thermal inertia of the thermal contact sensor in an idle state and in contact with the skin, comprising:
        heating the can-like housing with the heater;
        measuring the time it takes the heater to raise the temperature of the thermal contact sensor from 15° C. to 38° C.;
        if the elapsed time it takes the heater to raise the temperature of the thermal contact sensor is less than 400 msec, determining that there is no contact of the thermal contact sensor with the skin; and
        if the elapsed time it takes the heater to raise the temperature of the thermal contact sensor is more than 600 msec, determining that there is a contact of the thermal contact sensor with the skin.

2. The method of thermal contact detection of claim 1, wherein operating the thermal contact sensor in the first mode further comprises:
    attaching securely and firmly the metal frame, and the thermal contact sensor to the skin; and
    if the sensed sensor temperature is 20° C. or more, determining a presence of contact of the thermal contact sensor with the skin; and
    if the sensed temperature is 15° C. or less, determining an absence of contact of the thermal contact sensor with the skin.

3. The method of thermal contact detection of claim 1, wherein operating the thermal contact sensor in the first mode further comprises: using an internal processor to operate the heater to maintain the temperature difference between the skin and the metal frame.

4. The method of thermal contact detection of claim 1, wherein operating the thermal contact sensor in the first mode further comprises: using an internal processor to operate the heater in pulse mode, in a cycle where the heater is on for two seconds and is off for next two seconds.

5. The method of thermal contact detection of claim 4, wherein operating the thermal contact sensor in the first mode further comprises: sensing and transmitting a measured temperature of the thermal contact sensor when the heater is off.

6. The method of thermal contact detection of claim 1, wherein operating the thermal contact sensor in the second mode further comprises
    operating the heater in closed-loop control mode to maintain the thermal contact sensor at a temperature of 38° C.; and
    if there is an increase in electric power consumed by the heater, determining there is contact of the thermal contact sensor with the skin.

7. The method of thermal contact detection of claim 1, wherein the metal frame comprises stainless steel.

8. The method of thermal contact detection of claim 1, wherein operating the thermal contact sensor in one of the first mode, the second mode and the third mode consists of operating the thermal contact sensor in the first mode.

9. The method of thermal contact detection of claim 1, wherein operating the thermal contact sensor in one of the first mode, the second mode and the third mode consists of operating the thermal contact sensor in the second mode.

10. The method of thermal contact detection of claim 1, wherein operating the thermal contact sensor in one of the first mode, the second mode and the third mode consists of operating the thermal contact sensor in the third mode.

* * * * *